United States Patent [19]
Hirata et al.

[11] Patent Number: 6,166,224
[45] Date of Patent: Dec. 26, 2000

[54] METHOD FOR RACEMIZATION OF OPTICALLY ACTIVE AZETIDINE-2-CARBOXYLATE

[75] Inventors: Norihiko Hirata; Isao Kurimoto, both of Suita, Japan

[73] Assignee: Sumitomo Chemical Company, Limited, Osaka, Japan

[21] Appl. No.: 09/311,266

[22] Filed: May 14, 1999

[30] Foreign Application Priority Data

May 14, 1998 [JP] Japan .................................. 10-132145

[51] Int. Cl.⁷ ................................................ C07D 205/04
[52] U.S. Cl. ............................................................ 548/953
[58] Field of Search ............................................. 548/953

[56] References Cited

U.S. PATENT DOCUMENTS

| | | | |
|---|---|---|---|
| 5,183,939 | 2/1993 | Jansen et al. ............................ | 564/302 |
| 5,880,291 | 3/1999 | Ushio et al. ............................. | 548/953 |
| 6,017,956 | 1/2000 | Iwasawa et al. ........................ | 514/510 |

FOREIGN PATENT DOCUMENTS

| | | |
|---|---|---|
| 0 489 682 | 6/1992 | European Pat. Off. . |
| 0 827 954 | 3/1998 | European Pat. Off. . |
| WO 98/02417 | 1/1998 | WIPO . |
| WO 98/02568 | 1/1998 | WIPO . |

OTHER PUBLICATIONS

XP 002112278 abstract (Derwent Publication) "Racemization of optically active amino acids", which is an abstract of JP-A-39-26381, published on Nov. 9, 1964.

Starmans et al., Enzymatic resolution of methyl N-alkyl-azetidine-2-carboxylates by *Candida antarctia* lipase-mediated ammoniolysis, p 429–435, Apr. 17, 1985.

*Primary Examiner*—Cecilia Tsang
*Assistant Examiner*—Sonya N. Wright
*Attorney, Agent, or Firm*—Sughrue, Mion, Zinn, Macpeak & Seas, PLLC

[57] ABSTRACT

A method for racemization of an optically active N-substituted azetidine-2-carboxylic acid ester of the formula (1):

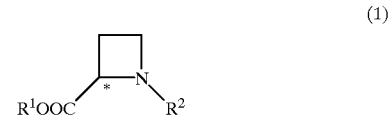

(1)

wherein * represents an asymmetric carbon atom, $R^1$ represents an aryl, $R^2$ represents a saturated hydrocarbon group which may be substituted, which is characterized by heating the ester at 100° C. or higher, or subjecting the ester to contact with a basic compound selected from an alkali metal hydride, an alkali metal alcoholate of tertiary alcohol and an organic amine.

23 Claims, No Drawings

METHOD FOR RACEMIZATION OF OPTICALLY ACTIVE AZETIDINE-2-CARBOXYLATE

BACKGROUND OF THE INVENTION

1. Field of the Invention

The present invention relates to a method for racemization of optically active N-substituted azetidine-2-carboxylic acid esters.

2. Description of the Related Art

An optically active N-substituted azetidine-2-carboxylic acid ester has been known as a useful intermediate for the production of pharmaceuticals and has been produced by an optical resolution as disclosed in WO98/02568 or EP827954 from a racemic mixture of the ester.

It has also been known that after resolution of a desired enantiomer of the N-substituted azetidine-2-carboxylic acid ester, the other enantiomer of the ester has been usually discarded with the exception of an optically active N-benzoyl azetidine-2-carboxylic acid ester which was susceptible of racemization for a further optical resolution.

SUMMARY OF THE INVENTION

An object of the invention is to provide a convenient racemization method that enables the reuse of an optically active N-substituted azetidine-2-carboxylic acid ester having a substituent group other than a benzoyl group on its N atom which has not been utilized so far. The present invention is beneficial from a economical viewpoint and result in reduction of waste in a production process.

DESCRIPTION OF THE PREFERRED EMBODIMENTS

The present invention provides a method for racemization of an optically active N-substituted azetidine-2-carboxylic acid ester of the formula (1):

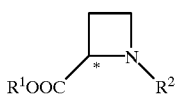

(1)

wherein * represents an asymmetric carbon atom, $R^1$ represents an optionally substituted aryl group, a saturated hyrodcarbon group which may be substituted with an optionally substituted aryl group, or an unsaturated hydrocarbon group, $R^2$ represents a saturated hydrocarbon group which may be substituted with an aryl group, an optionally substituted unsaturated hydrocarbon group, an alkyloxycarbonyl group which may be substituted, an alkenyloxycarbonyl group, or an optionally substituted sulfonyl group, which comprises:

heating the ester of the formula (1) at 100° C. or higher, or subjecting the ester to contact with a basic compound selected from an alkali metal hydride, an alkali metal alkoxide of a tertiary alcohol or an organic amine.

The optically active N-substituted azetidine-2-carboxylic acid ester of the formula (1) will be explained first.

Examples of the optionally substituted aryl group for $R^1$ include a phenyl group which may be substituted with a substituent selected from a halogen atom, ($C_1$–$C_3$) alkyl, ($C_1$–$C_3$) alkoxy and nitro.

Examples of the saturated hydrocarbon which may be substituted with an optionally substituted aryl group(s) for $R^1$ include ($C_1$–$C_5$) alkyl groups such as a methyl group, an ethyl group, an n-propyl group, an i-propyl group, an n-butyl group, an i-butyl group, a sec-butyl group, a t-butyl group, a benzyl group, a p-methoxybenzyl group, an o-nitrobenzyl group, a benzhydryl group and a triphenylmethyl group.

The unsaturated hydrocarbon group for $R^1$ includes an ($C_3$–$C_6$) alkenyl group such as an allyl group and 3-butenyl group and the like.

Examples of the saturated hydrocarbon group which may be substituted with an optionally substituted aryl group(s) for $R^2$ include:

an ($C_1$–$C_6$) alkyl group such as a methyl group, an ethyl group, an ($C_7$–$C_{20}$) aralkyl group which may be substituted with a halogen atom, an ($C_1$–$C_3$) alkyl group, an ($C_1$–$C_3$) alkoxy group or a nitro group such as a benzyl group, a p-methoxybenzyl group, an α-phenylethyl group, a β-phenylethyl group, a phenylpropyl group, a benzhydryl group and a triphenylmethyl group.

Examples of the unsaturated hydrocarbon group for $R^2$ include an ($C_3$–$C_6$) alkenyl group such as an allyl group.

The saturated hydrocarbon groups or unsaturated hydrocarbon groups for $R^2$ may be substituted with at least one substituent selected from an ($C_1$–$C_3$) alkoxy group and a halogen atom (fluorine atom, chlorine atom, bromine atom or iodine atom).

Examples of the alkyloxycarbonyl group which may be substituted for $R^2$ include:

an $C_1$–$C_6$ alkyloxycarbonyl group which may be substituted with an aryl group (e.g., phenyl, naphthyl), a halogen atom, an alkoxy group, or a nitro group wherein the aryl group may be substituted with a halogen atom, group, an ($C_1$–$C_3$) alkyl group, an ($C_1$–$C_3$) alkoxy group, or a nitro group. Specific examples thereof include a t-butoxycarbonyl group, a trichloroethyloxycarbonyl group, benzyloxycarbonyl group, a p-methoxybenzyloxycarbonyl group and a 2-phenylethyloxycarbonyl group.

Examples of the ($C_2$–$C_6$) alkenyloxycarbonyl group for $R^2$ include a vinyloxycarbonyl group, an allyloxycarbonyl group and a 1-isopropylallyloxycarbonyl group.

The optionally substituted sulfonyl group includes benzenesulfonyl groups which may be substituted with an ($C_1$–$C_3$) alkyl group, an ($C_1$–$C_3$) alkoxy group or a nitro group, specific examples of which include a benzenesulfonyl group, a p-toluenesulfonyl group, a p-methoxybenzenesulfonyl group and an o-nitrobenzenesulfonyl group.

The substituent $R^2$ may have an asymmetric carbon atom.

Examples of the substituent $R^2$ having an axymmetric carbon atom include:

an (S)-methylbenzyl group, an (R)-methylbenzyl group, an (S)-1-phenylpropyl group, an (R)-1-phenylpropyl group, an (S)-1-(p-tolyl)ethyl group, an (R)-1-(p-tolyl)ethyl group, an (S)-1-(p-chlorophenyl)ethyl group, an (R)-1-(p-chlorophenyl)ethyl group, an (S)-1-(2,4-dichlorophenyl)ethyl group, an (R)-1-(2,4-dichlorophenyl)ethyl group, an (S)-1-(p-methoxyphenyl)ethyl group, an (R)-1-(p-methoxyphenyl)ethyl group, an (S)-1-(4-hydroxyphenyl)ethyl group, and an (R)-1-(4-hydroxyphenyl)ethyl group.

Examples of the optically active N-substituted azetidine-2-carboxylic acid ester (1) include:
methyl N-methylazetidine-2-carboxylate, methyl N-ethylazetidine-2-carboxylate,
methyl N-benzylazetidine-2-carboxylate,
methyl N-p-methoxylbenzylazetidine-2-carboxylate,
methyl N-[(S)-1-methylbenzyl]-azetidine-2-carboxylate,
methyl N-[(R)-1-methylbenzyl]-azetidine-2-carboxylate,
methyl N-[(S)-1-phenylpropyl]-azetidine-2-carboxylate,
methyl N-[(R)-1-phenylpropyl]-azetidine-2-carboxylate,
methyl N-[(S)-1-p-tolyl)ethyl]-azetidine-2-carboxylate,
methyl N-[(R)-1-(p-tolyl)ethyl]-azetidine-2-carboxylate,
methyl N-[(S)-1-p-chlorophenyl)ethyl]-azetidine-2-carboxylate,
methyl N-[(R)-1-chlorophenyl)ethyl]-azetidine-2-carboxylate,
methyl N-[(S)-1-(2,4-dichlorophenyl)ethyl]-azetidine-2-carboxylate,
methyl N-[(R)-1-(2,4-dichlorophenyl)ethyl]-azetidine-2-carboxylate,
methyl N-[(S)-1-(2-methoxyphenyl)ethyl]-azetidine-2-carboxylate,
methyl N-[(R)-1-(p-methoxyphenyl)ethyl]-azetidine-2-carboxylate,
methyl N-[(S)-1-(p-hydroxyphenyl)ethyl]-azetidine-2-carboxylate,
methyl N-[(R)-1-(p-hydroxyphenyl)ethyl]-azetidine-2-carboxylate,
methyl N-β-phenylethylazetidine-2-carboxylate,
methyl N-phenylpropylazetidine-2-carboxylate,
methyl N-benzhydrylazetidine-2-carboxylate,
methyl N-triphenylmethylazetidine-2-carboxylate,
methyl N-allylazetidine-2-carboxylic acid ester,
methyl N-t-butoxycarbonylazetidine-2-carboxylate,
methyl N-trichloroethyloxycarbonylazetidine-2-carboxylate,
methyl N-benzyloxycarbonylazetidine-2-carboxylate,
methyl N-p-methoxybenzyloxycarbonylazetidine-2-carboxylate,
methyl N-2-phenylethyloxycarbonylazetidine-2-carboxylate,
methyl N-vinyloxycarbonylazetidine-2-carboxylate,
methyl N-allyloxycarbonylazetidine-2-carboxylate,
methyl N-1-isopropylallyloxycarbonylazetidine-2-carboxylate,
methyl N-benzenesulfonylazetidine-2-carboxylate,
methyl N-p-toluenesulfonylazetidine-2-carboxylate,
methyl N-p-methoxybenzenesulfonylazetidine-2-carboxylate,
methyl N-o-nitrobenzenesulfonylazetidine-2-carboxylate, and
compounds having, as an alkyl residue of the ester substituent, a group selected from an ethyl group, a n-propyl group, an isopropyl group, a n-butyl group, an isobutyl group, a sec-butyl group, a t-butyl group, a benzyl group, a p-methoxybenzyl group, an o-nitrobenzyl group, a benzhydryl group, a triphenylmethyl group, an allyl group and a 3-butenyl group in place of the methyl group of the above listed compounds.

The optically active N-substituted azetidine-2-carboxylic acid ester of the formula (1) which is enriched in one optical isomer may be used in the present invention irrespective of the degree of enantiomeric excess of a specific optical isomer contained therein.

The ester to be used in the racemization process of the present invention may be purified in advance by distillation, column chromatography and the like, if necessary, or may be used as a mixture of isomers which is rich in one isomer recovered from a resolution procedure such as optical resolution, enzymatic resolution and the like, if necessary.

In the racemization method of the present invention, when the substituent $R^2$ is a substituent having an asymmetric carbon atom, racemization of the asymmetric carbon atom marked with * in the formula (1) proceeds with high selectivity to produce a diastereomer mixture, which can be separated by a conventional procedure such as column chromatography, optical resolution using an optically active acid and the like.

The method for racemization of the optically active N-substituted azetidine-2-carboxylic acid ester of the formula (1) is usually carried out by heating it at 100° C. or higher in the presence or absence of an organic solvent.

A basic compound may be used in the racemization reaction. Examples of the basic compound include those listed below. When the basic compound is used, the organic solvent is usually used together. On the other hand, when no basic compound is used, the reaction can be conducted without an organic solvent.

Examples of the organic solvent include aromatic compounds such as benzene, toluene, ethylbenzene, xylene and chlorobenzene, hydrocarbons such as hexane, cyclohexane, heptane and isooctane, ether such as t-butyl methyl ether, isopropyl ether, tetrahydrofuran and dioxane, alcohol such as methanol, ethanol, isopropanol, n-butanol and t-butanol, ketones such as acetone and 2-butanone, nitriles such as acetonitrile, amides such as N,N-dimethylformamide and N,N-dimethylacetamide, sulfoxides such as dimethyl sulfoxide, and mixtures thereof.

The amount of the organic solvent used is usually not more than 100 parts, preferably not more than 20 parts, more preferably not more than 10 parts by weight of the ester of the formula (1).

The optically active N-substituted azetidine-2-carboxylic acid ester of the formula (1) is usually heated at a temperature of 100° C. or higher. More specifically, the temperature is 100° C. to 300° C., preferably 100° C. to 250° C., more preferably 100° C. to 200° C.

The present method of racemization of the optically active N-substituted azetidine-2-carboxylic acid ester of the formula (1) can also be carried out by contacting the ester of the formula (1) with a basic compound selected from an alkali metal hydride, an alkali metal alkoxide of tertiary alcohol and an organic amine.

Examples of the alkali metal hydrides include sodium hydride, potassium hydride and lithium hydride.

Examples of the alkaline earth metal hydride include calcium hydride.

Examples of the alkali metal alkoxide of tertiary alcohol include potassium t-butoxide.

Examples of the organic amines includes a tertiary amine such as triethylamine, diisopropylethylamine, 1,5-diazabicyclo[4.3.0]non-5-ene, 1,8-diazabicyclo[5.4.0]-7-undencene and N-methylmorpholine.

The basic compound may be used either alone or in combination of two or more of them. Particularly, the alkali metal hydrides are preferably used.

The amount of the basic compound used is not particularly limited, but is usually 0.01 to 10 mols, preferably 0.01 to 5 mols, more preferably 0.1 to 2 mols, per mol of the ester of the formula (1).

The ester of the formula (1) is usually contacted with the basic compound at −20° C. to 200° C., preferably 0° C. to 150° C., more preferably 20° C. to 100° C.

The racemized N-substituted azetidine-2-carboxylic acid ester thus obtained by the present invention can be reused in a optical resolution process to produce the enantiomer of the optically active N-substituted azetidine-2-carboxylic acid ester of the formula (1) after being subjected to a conventional procedure, for example, neutralization with acidic water or the like, followed by distillation of the solvent, if necessary.

According to the method of the present invention, the optically active N-substituted azetidine-2-carboxylic acid esters (1) can be readily and efficiently racemized.

EXAMPLES

The present invention will be explained in detail by the following Examples which should not be construed to limit the invention thereto.

Example 1

5.9 g (2R isomer:2S isomer=94:6) of methyl N-[(S)-phenylethyl]-azetidine-2-carboxylic acid ester was heated to 170° C. and kept at the temperature for 8 hours. The gas chromatography analysis of the oil-like product showed that methyl N-[(S)-phenylethyl]-azetidine-2-carboxylic acid ester was obtained in a yield of 71.7%. The diastereomeric ratio (2R isomer:2S isomer) was 42:58.

Example 2

4.3 g (2R isomer:2S isomer=92:8) of methyl N-[(S)-phenylethyl]-azetidine-2-carboxylic acid ester was heated to 190° C. and kept at that temperature for 10 hours. The gas chromatography analysis of the oil-like product showed that methyl N-[(S)-phenylethyl]-azetidine-2-carboxylic acid ester was obtained in a yield of 70.4%. The diastereomeric ratio (2R isomer:2S isomer) was 45:55.

Example 3

13.4 g (2R isomer:2S isomer=93:7) of methyl N-[(S)-phenylethyl]-azetidine-2-carboxylic acid ester was heated to 190° C. and kept at that temperature for 10 hours. The gas chromatography analysis of the oil-like product showed that methyl N-[(S)-phenylethyl]-azetidine-2-carboxylic acid ester was obtained in a yield of 73.8%. The diastereomeric ratio (2R isomer:2S isomer) was 50:50.

Example 4

To a solution obtained by dissolving 20.0 g (2R isomer:2S isomer=93:7) of methyl N-[(S)-phenylethyl]-azetidine-2-carboxylic acid ester in 73.6 g of toluene was added 3.65 g of sodium hydride (an oil suspension containing sodium hydride in a content of about 60%) at room temperature. The resulting mixture was heated up to 80° C., and kept at that temperature for 8 hours. To the resulting solution were added dropwise 20 g of water and then 24.8 g of a 35% aqueous hydrochloric acid solution to adjust the pH value to 0.6 while being cooled in ice. The mixture was thereafter separated into an oil layer and a water layer. The water layer was washed with 40 g of toluene, and then another 40 g of toluene was added thereto. To the resulting mixture was added dropwise 33.9 g of a 20% aqueous sodium hydroxide solution to adjust the pH value to 6.3, and then the mixture was separated into an oil layer and a water layer. The oil layer was washed with 40 g of water, and the solvent was then distilled from the oil layer. The gas chromatography analysis of the oil-like product showed that methyl N-[(S)-phenylethyl]-azetidine-2-carboxylic acid ester was obtained in a yield of 94.6%. The diastereomeric ratio (2R isomer:2S isomer) was 42:58.

Example 5

To a solution obtained by dissolving 7.0 g (2R isomer:2S isomer=93:7) of methyl N-[(S)-phenylethyl]-azetidine-2-carboxylic acid ester in 25.7 g of toluene was added 1.28 g of sodium hydride (an oil suspension containing sodium hydride in a content of about 60%) at room temperature. The resulting mixture was heated up to 70° C., and kept at that temperature for 10 hours. To the resulting solution were added dropwise 7 g of water and then 9.8 g of a 35% aqueous hydrochloric acid solution to adjust the pH value to 1.0 with being cooled in ice. The mixture was thereafter separated into an oil layer and a water layer. The water layer was washed with 14 g of toluene, and then another 14 g of toluene was added thereto. To the resulting mixture was added dropwise 12.0 g of a 20% aqueous sodium hydroxide solution to adjust the pH value to 6.1, and then the mixture was separated into an oil layer and a water layer. The oil layer was washed with 14 g of water, and the solvent was then distilled from the oil layer. The gas chromatography analysis of the oil-like product showed that methyl N-[(S)-phenylethyl]-azetidine-2-carboxylic acid ester was obtained in a yield of 96.7%. The diastereomeric ratio (2R isomer:2S isomer) was 44:56.

Example 6

To a solution obtained by dissolving 7.0 g (2R isomer:2S isomer=93:7) of methyl N-[(S)-phenylethyl]-azetidine-2-carboxylic acid ester in 25.7 g of toluene was added 1.28 g of sodium hydride (an oil suspension containing sodium hydride in a content of about 60%) at room temperature. The resulting mixture was heated up to 60° C., and kept at that temperature for 20 hours. To the resulting solution were added dropwise 7 g of water and then 9.8 g of a 35% aqueous hydrochloric acid solution to adjust the pH value to 1.1 with being cooled in ice. The mixture was thereafter separated into an oil layer and a water layer. The water layer was washed with 14 g of toluene, and then another 14 g of toluene was added thereto. To the resulting mixture was added dropwise 11.8 g of a 20% aqueous sodium hydroxide solution to adjust the pH value to 6.3, and then the mixture was separated into an oil layer and a water layer. The oil layer was washed with 14 g of water, and the solvent was then distilled from the oil layer. The gas chromatography analysis of the oil-like product showed that methyl N-[(S)-phenylethyl]-azetidine-2-carboxylic acid ester was obtained in a yield of 92.7%. The diastereomeric ratio (2R isomer:2S isomer) was 44:56.

Example 7

To a solution obtained by dissolving 5.0 g (2R isomer:2S isomer=100:0) of benzyl N-[(S)-phenylethyl]-azetidine-2-carboxylic acid ester in 20.0 g of toluene was added 0.74 g of sodium hydride (an oil suspension containing sodium hydride in a content of about 60%) at room temperature. The resulting mixture was heated up to 80° C., and kept at that temperature for 3 hours. To the resulting solution were added dropwise 5 g of water and then 2.1 g of a 35% aqueous hydrochloric acid solution to adjust the pH value to 6.5 with being cooled in ice. The mixture was thereafter separated into an oil layer and a water layer. The oil layer was washed with 5 g of water, and the solvent was then distilled from the oil layer. The gas chromatography analysis of the oil-like product showed that benzyl N-[(S)-phenylethyl]-azetidine-2-carboxylic acid ester was obtained in a yield of 81.8%. The diastereomeric ratio (2R isomer:2S isomer) was 41:59.

Example 8

To a solution obtained by dissolving 3.0 g (2R isomer:2S isomer=100:0) of methyl N-benzylazetidine-2-carboxylic acid ester in 12.1 g of toluene was added 0.65 g of sodium hydride (an oil suspension containing sodium hydride in a content of about 60%) at room temperature. The resulting mixture was heated up to 80° C., and kept at that temperature for 3 hours. To the resulting solution were added dropwise 10 g of water and then 1.5 g of a 35% aqueous hydrochloric acid solution to adjust the pH value to 6.5 with being cooled in ice. The mixture was thereafter separated into an oil layer and a water layer. The oil layer was washed with 5 g of water, and the solvent was then distilled from the oil layer. The gas chromatography analysis of the oil-like product showed that methyl N-benzylazetidine-2-carboxylic acid ester was obtained in a yield of 75.0%. The diastereomeric ratio (2R isomer:2S isomer) was 50:50.

Example 9

To a solution obtained by dissolving 1.0 g (pure content: 0.8 g; 2R isomer:2S isomer=34:66) of methyl N-[(R)-phenylethyl]-azetidine-2-carboxylic acid ester in a mixed solvent of 15 ml of t-butyl methyl ether and 5 ml of N,N-dimethylformamide was added 0.16 g of sodium hydride (an oil suspension containing sodium hydride in a content of about 60%) at room temperature. The resulting mixture was kept at that temperature for 5 hours. The gas chromatography analysis of the resulting solution showed that the diastereomer ratio (2R isomer:2S isomer) of methyl N-[(R)-phenylethyl]-azetidine-2-carboxylic acid ester was 56:44. The solution was heated up to 45° C. and kept at that temperature for 3 hours. The diastereomeric ratio (2R isomer:2S isomer) changed to 60:40.

The N-substituted azetidine-2-carboxylic acid esters obtained by the above Examples can be optically resolved in a technique such as that described below.

Reference Example 1

18.9 g (2R isomer:2S isomer=42:58) of methyl N-[(S)-phenylethyl]-azetidine-2-carboxylic acid ester obtained in Example 4 was dissolved in a mixed solvent of 9.6 g toluene and 2.7 g of methanol, and then heated up to 60° C. To the solution was added a small amount of L-tartrate of methyl N-[(S)-phenylethyl]-azetidine-2-carboxylic acid ester as a seed crystal, and then a solution of 13.6 g of L-tartaric acid in 24.6 g of methanol dropwise at 60° C. over 2 hours. The resulting solution was cooled down to 0° C. in the course of 3 hours, and then kept at that temperature for 3 hours. The crystal formed was collected by filtration and L-tartrate of methyl N-[(S)-phenylethyl]-azetidine-2-carboxylic acid ester (2R isomer:2S isomer=0.2:99.8) was obtained in a yield of 48.6%.

Comparative Example 1

(Experiment Similar to that Described in WO98/02568)

5.20 g (23.7 mmol) of methyl N-[(S)-phenylethyl]-azetidine-2-(S)-carboxylic acid ester (100% d.e.) was dissolved in 200 ml of methanol. To the solution was added 0.26 g (4.8 mmol) of sodium methoxide, and then the resulting solution was refluxed for 24 hours. To the reaction mixture was added acetic acid until the pH value became 6.5, and then the solvent was distilled off. The residue was dissolved in ethyl acetate and washed with water. Racemization of the ester was not observed by an analysis carried out 8 hours after the beginning of the reaction. 5.04 g of the ester (98.9 % d.e.) was recovered with retention of the configuration as a pale yellow oil after removal of the solvent under reduced pressure.

What is claimed is:

1. A method for racemization of an optically active N-substituted azetidine-2-carboxylic acid ester of the formula (1):

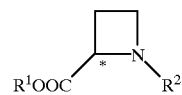

(1)

wherein * represents an asymmetric carbon atom $R^1$ represents an optionally substituted aryl group, a saturated hydrocarbon group which may be substituted with an optionally substituted aryl group, or an unsaturated hydrocarbon group, $R^2$ represents a saturated hydrocarbon group which may be substituted, an optionally substituted unsaturated hydrocarbon group, an alkyloxycarbonyl group which may be substituted, an alkenyloxycarbonyl group, or an optionally substituted sulfonyl group, which comprises subjecting the ester, to contact with a basic compound selected from an alkali metal hydride, an alkaline earth metal hydride, an alkali metal alkoxide of tertiary alcohol or an organic amine.

2. The method according to claim 1, wherein both $R^1$ and $R^2$ are a saturated hydrocarbon group which may be substituted with an aryl group, or an unsaturated hydrocarbon group.

3. The method according to claim 1, wherein the racemization reaction temperature is not higher than 200° C.

4. The method according to claim 2, wherein the racemization reaction temperature is not higher than 200° C.

5. The method according to claim 1, wherein the basic compound is an alkali metal hydride.

6. The method according to claim 2, wherein the basic compound is an alkali metal hydride.

7. The method according to claim 3, wherein the basic compound is an alkali metal hydride.

8. The method according to claim 1, which further comprises subjecting the product obtained by racemization to optical resolution to obtain an enantiomer of the optically active N-substituted azetidine-2-carboxylic acid ester of the formula (1).

9. A method for racemization of an optically active N-substituted azetidine-2-2-carboxylic acid ester of the formula (1):

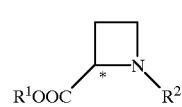

(1)

wherein * represents an asymmetric carbon atom, $R^1$ represents an optionally substituted aryl group, a saturated hydrocarbon group which may be substituted with an optionally substituted aryl group, or an unsaturated hydrocarbon group, $R^2$ represents a saturated hydrocarbon group which may be substituted, an optionally substituted unsaturated hydrocarbon group, an alkyloxycarbonyl group which may be substituted, an alkenyloxycarbonyl group, or an optionally substituted sulfonyl group, which comprises heating the ester of the formula (1) at 100° C. or higher in the absence of a base.

10. The method according to claim 9, wherein both $R^1$ and $R^2$ are a saturated hydrocarbon group which may be substituted with an aryl group, or an unsaturated hydrocarbon group.

11. The method according to claim 9, wherein the racemization reaction temperature is not higher than 200° C.

12. The method according to claim 10, wherein the racemization reaction temperature is not higher than 200° C.

13. The method according to claim 9, which further comprises subjecting the product obtained by racemization to optical resolution to obtain an enantiomer of the optically active N-substituted azetidine-2-carboxylic acid ester of the formula (1).

14. A method for racemization of an optically active N-substituted azetidine-2-carboxylic acid ester of the formula (1):

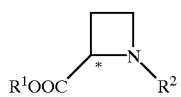
(1)

wherein * represents an asymmetric carbon atom,
$R^1$ represents an optionally substituted aryl group, a saturated hydrocarbon group which may be substituted with an optionally substituted aryl group, or an unsaturated hydrocarbon group,
$R^2$ represents a saturated hydrocarbon group which may be substituted, an optionally substituted unsaturated hydrocarbon group, an alkyloxycarbonyl group which may be substituted, an alkenyloxycarbonyl group, or an optionally substituted sulfonyl group,
which comprises heating the ester of the formula (1) at 100° C. or higher.

15. The method according to claim 14, wherein both $R^1$ and $R^2$ are a saturated hydrocarbon group which may be substituted with an aryl group, or an unsaturated hydrocarbon group.

16. The method according to claim 14, wherein the racemization reaction temperature is not higher than 200° C.

17. The method according to claim 15, wherein the racemization reaction temperature is not higher than 200° C.

18. The method according to claim 14, wherein the ester is contacted with a basic compound.

19. The method according to claim 18, wherein the base compound is selected from an alkali metal hydride, an alkaline earth metal hydride, an alkali metal alkoxide of tertiary alcohol, or an organic amine.

20. The method according to claim 19, wherein the basic compound is an alkali metal hydride.

21. The method according to claim 19, wherein both $R^1$ and $R^2$ are a saturated hydrocarbon group which may be substituted with an aryl group, or an unsaturated hydrocarbon group.

22. The method according to claim 19, wherein the racemization temperature is not higher than 200° C.

23. The method according to claim 19, which further comprises subjecting the product obtained by racemization to optical resolution to obtain an enantiomer of the optically active N-substituted azetidine-2-carboxylic acid ester of the formula (1).

* * * * *